US007935498B2

(12) United States Patent
Christie

(10) Patent No.: US 7,935,498 B2
(45) Date of Patent: May 3, 2011

(54) METHODS FOR IDENTIFYING PATIENTS WITH INCREASED RISK OF AN ADVERSE CARDIOVASCULAR EVENT

(75) Inventor: Douglas J. Christie, Newark, DE (US)

(73) Assignee: Siemens Healthcare Diagnostics Inc., Deerfield, IL (US)

( * ) Notice: Subject to any disclaimer, the term of this patent is extended or adjusted under 35 U.S.C. 154(b) by 463 days.

(21) Appl. No.: 11/483,028

(22) Filed: Jul. 7, 2006

(65) Prior Publication Data

US 2008/0009024 A1   Jan. 10, 2008

(51) Int. Cl.
*C12Q 1/56* (2006.01)
(52) U.S. Cl. ..... 435/13; 435/7.21; 435/287.1; 514/13.7; 514/14.9
(58) Field of Classification Search ............ 435/13
See application file for complete search history.

(56) References Cited

U.S. PATENT DOCUMENTS

| 5,256,538 | A | 10/1993 | Aiken et al. |
| 6,124,101 | A | 9/2000 | Coughlin |
| 6,210,877 | B1 | 4/2001 | Francis et al. |
| 6,410,337 | B1 | 6/2002 | Brady et al. |
| 6,780,605 | B1 | 8/2004 | Frostegard |
| 2003/0100036 | A1 | 5/2003 | Vojdani |
| 2003/0109420 | A1 | 6/2003 | Valkirs et al. |
| 2003/0124615 | A1 | 7/2003 | Ens |
| 2004/0115735 | A1 | 6/2004 | Yusuf et al. |
| 2004/0131500 | A1 | 7/2004 | Chow |
| 2004/0185516 | A1 | 9/2004 | Frostegard |
| 2005/0019742 | A1 | 1/2005 | Jennings et al. |
| 2005/0181386 | A1 | 8/2005 | Diamond et al. |
| 2005/0196748 | A1 | 9/2005 | Ericson |
| 2005/0250156 | A1 | 11/2005 | Shebuski et al. |
| 2005/0255534 | A1 | 11/2005 | Ericson |

OTHER PUBLICATIONS

Frossard et al. "Platelet Function Predicts Myocardial Damage in Patients with Acute Myocardial Infarction". Circulation (2004) 110: 1392-1397.
Wang et al. "Incidence of Aspirin Nonresponsiveness Using the Ultegra Rapid Platelet Function Assay-ASA". Am J Cardiol. (2003) 92: 1492-1494.
Alberts et al. "Antiplatelet Effect of Aspirin in Patients with Cerebrovascular Disease". Stroke (2004)35: 175-178.
Chen, W-H et al. "Aspirin Resistance is Associated with a High Incidence of Myonecrosis After Non-urgent Percutaneous Coronary Intervention Despite Clopidogrel Pretreatment". J. Am. Coll. Cardoil. (2004)43: 1127-1129.
Macchi et al. "Resistance to Aspirin in Vitro is Associated with Increased Platelet Sensitivity to Adenosine Diphosphate". Throm Res. (2002)107: 45-49.
Jilma, B. "Platelet Function Analyzer (PFA-100): A Tool to Quantify Congenital or Acquired Platelet Dysfunction". J. Lab. Clin. Med. (2001)138: 152-163.
Gum et al. "A Prospective, Blinded Determination of the Natural History of Aspirin Resistance Among Stable Patients with Cardiovascular Disease". J. Am Coll. Cardiol. (2003)41: 961-965.
Gum et al. "Profile and Prevalence of Aspirin Resistance in Patients with Cardiovascular Disease". J. Am Coll. Cardiol. (2001) 88: 230-235.
Furman et al. "Increased Platelet Reactivity and Circulating Monocyte-platelet Aggregates in Patients with Stable Coronary Artery Disease". J. Am Coll. Cardiol. (1998)31: 352-358.
Macchi et al. "Resistance in vitro to Low-dose Aspirin is Associated with Platelet P1A1 (GP IIIa) Polymorphism but not with 807T (GPla/IIa) and C-5T Kosak (GP Ibα) Polymorphisms". J. Am Coll. Cardiol. (2003)42: 1115-1119.
Matetzky et al. "Clopidogrel Resistance is Associated with Increased Risk of Recurrent Atherothrombotic Events in Patients with Acute Myocardial Infarction". Circulation (2004)109: 3171-3175.
Eikelboom et al. "Aspirin-resistant Thromboxane Biosynthesis and the Risk of Myocardial Infarction, Stroke or Cardiovascular Death in Patients at High Risk for Cardiovascular Events". Circulation (2002)105: 1650-1655.
Grundmann et al: "Aspirin Non-responder status in patients with recurrent cerebral ischemic attacks." Journal of Neurology, vol. 250, No. 1, Jan. 2003, pp. 63-66, XP002527965, ISSN: 0340-5354.
Frelinger et al: "Patients with coronary artery disease have an increased incidence of aspirin resistance: Association of PFA-100 closure time with clinical findings", BLOOD, vol. 104, No. 11, Part 1, Nov. 2004. Page 514A, XP009116980 & 46th Annual Meeting of the American-Society-of-Hemotolgy; San Diego, CA; Dec. 4-7, 2004 ISSN: 0006-4971.
Gianetti, J. et al., "Platelet Activation Predicts Recurrent Ischemic Events After Percutaneous Coronary Angioplasty: A 6 Months Prospective Study", Thrombosis Research, (2006), vol. 118, pp. 487-493.

*Primary Examiner* — Jon P Weber
*Assistant Examiner* — Tiffany M Gough
(74) *Attorney, Agent, or Firm* — Theodore J. Leitereg

(57) ABSTRACT

Methods, compositions and kits are disclosed for identifying patients with an increased risk of experiencing an adverse cardiovascular event where the patient is undergoing aspirin antiplatelet therapy. A platelet-containing sample from the patient is evaluated for platelet hyperactivity and platelet hyperactivity in the sample is related to the patient's risk of an adverse cardiovascular event. In some embodiments the evaluation for platelet hyperactivity is carried out by assessing the function of platelets in the sample using a high shear platelet function test.

18 Claims, 1 Drawing Sheet

METHODS FOR IDENTIFYING PATIENTS WITH INCREASED RISK OF AN ADVERSE CARDIOVASCULAR EVENT

BACKGROUND

This invention relates to methods for identifying patients with increased risk of experiencing an adverse cardiovascular event. The invention also relates to the determination of platelet hyperactivity in a patient undergoing aspirin anti-platelet therapy as an indication of an increased risk of suffering a cardiovascular event.

The term "cardiovascular disease" refers to a class of diseases that involve the heart and/or blood vessels (arteries and veins), i.e., any disease that affects the cardiovascular system. Over fifty million Americans have cardiovascular problems, and most other Western countries face high and increasing rates of cardiovascular disease. It is the number one cause of death and disability in the United States and most European countries.

The role of platelets in mammalian physiology is extraordinarily diverse, but their primary role is in promoting hemostasis. When exposed to a damaged blood vessel, platelets will adhere to an exposed sub-endothelial matrix. Following the initial adhesion, various factors released at the site of injury such as thrombin, ADP and collagen activate the platelets. Once platelets are activated, a conformational change occurs in the platelet glycoprotein GPIIb/IIIa receptor allowing it to bind fibrinogen and/or von Willebrand factor. It is this binding of the multivalent fibrinogen and/or von Willebrand factor molecules by GPIIb/IIIa receptors on adjacent platelets that results in the recruitment of additional platelets to the site of injury and their aggregation to form a hemostatic plug or thrombus.

Questions of interest include whether to administer drugs that will block, or promote, clot formation, or whether to detect deficiencies in platelet function prior to surgical procedures. Platelets are known to play an active role in the development of cardiovascular disease (CVD). Consequently, therapeutic strategies to inhibit platelet function are extremely important.

Millions of people are taking aspirin, the oldest and most widely used platelet inhibiting agent, as therapy to reduce the risk of heart attacks and other cardiovascular events. These include persons that have previously suffered a cardiovascular event as well as those with elevated cholesterol, a family history of heart disease, or other risk factors for cardiovascular disease. Among those with risk factors, many persons that have had a heart attack or other cardiovascular event are prescribed some anti-platelet agent, usually aspirin. Aspirin (acetyl salicylic acid) effectively reduces the risk of secondary thrombotic events in individuals who have experienced angina, myocardial infarct, peripheral artery disease, or cerebrovascular ischemia. Aspirin also may reduce the risk of initial thrombotic events in healthy individuals and many healthy people without a recognized elevated risk of cardiovascular disease also take aspirin as a precaution. For this reason, many individuals, through physician prescriptions or self-medication, take aspirin on a regular basis for the primary or secondary prevention of thrombotic disease.

However, it is known that aspirin reduces ischemic vascular events by only about 22%. Poor responsiveness to aspirin, as measured by various laboratory tests, is associated with vascular ischemic disorders including myocardial infarction, coronary artery disease and stroke.

It would be desirable, therefore, to be able to determine the likelihood of a patient undergoing aspirin therapy to experience an adverse cardiovascular event. It would be desirable to identify patients with increased risk of a major adverse cardiovascular event even while undergoing aspirin therapy. The ability to identify high-risk individuals would allow physicians to focus preventive measures on those individuals, who may gain the greatest benefit, and would provide strong incentives for those at risk to comply with such approaches.

SUMMARY

One aspect of the present invention is a method for identifying a patient with an increased risk of experiencing an adverse cardiovascular event where the patient is undergoing aspirin antiplatelet therapy. A platelet-containing sample from the patient is evaluated for platelet hyperactivity and platelet hyperactivity in the sample is related to the patient's risk of an adverse cardiovascular event.

Another embodiment in accordance with the present invention is directed to a method for assessing the risk of an adverse cardiovascular event in a patient undergoing antiplatelet aspirin therapy. A platelet-containing sample from the patient is drawn under vacuum through a capillary so that it contacts a membrane comprising an aperture and platelets in the sample are activated by means of shear force. The membrane comprises a platelet aggregation stimulator. The time to formation of a platelet plug that blocks the aperture of the membrane is determined and the time to formation of a platelet plug is related to the patient's risk of an adverse cardiovascular event.

Another embodiment in accordance with the present invention is a method for assessing the risk of an adverse cardiovascular event in a patient undergoing antiplatelet aspirin therapy. A whole blood sample from the patient is drawn under vacuum through a capillary so that it contacts a membrane comprising an aperture and platelets in the sample are activated by means of shear force, wherein the membrane comprises a platelet aggregation stimulator. The time to formation of a platelet plug that blocks the aperture of the membrane is measured and is related to the patient's risk of an adverse cardiovascular event wherein the time to formation of a platelet plug is compared to a predetermined time. A time to formation of a platelet plug less than the predetermined time is indicative of an increased risk of the patient for an adverse cardiovascular event.

DESCRIPTION OF SPECIFIC EMBODIMENTS

Figure 1:
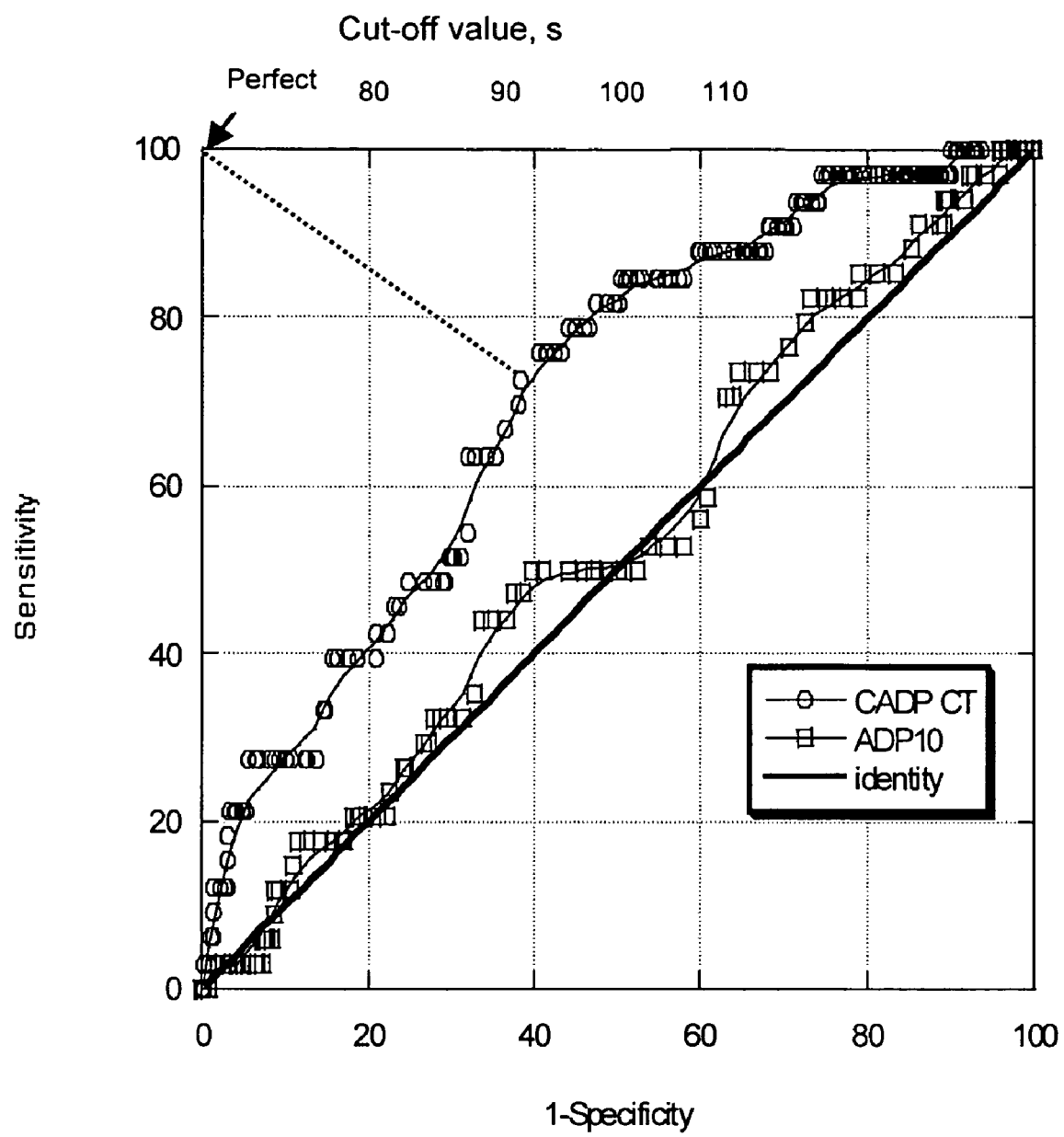
FIG. 1 is a sensitivity-specificity graph depicting platelet function test results versus the composite endpoint of death, myocardial infarction or cerebrovascular accident in aspirin sensitive patients with stable cardiovascular disease.

As mentioned above, in one embodiment the present invention is directed to methods for identifying a patient having an increased risk of experiencing an adverse cardiovascular event. The patients in question are those undergoing antiplatelet therapy with administration of aspirin. A platelet-containing sample from the patient is evaluated for platelet hyperactivity. The results of the evaluation are employed to assess the patient's risk of an adverse cardiovascular event. In general, platelet hyperactivity in the sample is an indication of an increased risk of an adverse cardiovascular event. Typically, the evaluation is carried out under high shear conditions in the presence of a platelet aggregation stimulator.

The adverse cardiovascular events include, by way of illustration and not limitation, arterial thrombotic events or vascular ischemic disorders including myocardial infarction, coronary artery disease, stroke, angina (stable and unstable), peripheral artery disease, cerebrovascular ischemia.

Patients undergoing aspirin therapy are those patients who are being treated with an effective amount of aspirin, i.e., an amount sufficient or effective to reduce the incidence of arterial thrombotic events and/or to prevent myocardial infarction, cerebrovascular thrombotic disease, and vascular death in individuals with stable angina, unstable angina, myocardial infarction, transient cerebral ischemia, peripheral vascular disease, thrombotic stroke, and the like. Typical doses for aspirin therapy may be between 30 and 325 mg/day.

A platelet-containing sample from a patient undergoing antiplatelet therapy is evaluated for platelet hyperactivity. The platelet-containing sample is any sample from the patient that contains platelets that can be evaluated for hyperactivity. In many instances the sample is whole blood or platelet rich plasma. The particular form of the platelet-containing sample may vary depending on the nature of the method for determining platelet hyperactivity.

Platelet hyperactivity in the context of the present disclosure means that the time to platelet plug formation in a given patient's platelet-containing samples is below an established cut-off value as determined from a sensitivity-specificity graph such as shown in FIG. 1.

In the example of FIG. 1, platelet hyperactivity is defined by a platelet plug formation time of less than 90 seconds. The extent that the platelets exhibit hyperactivity is related to the risk of a patient experiencing an adverse cardiovascular event. Generally, platelet hyperactivity, having a platelet plug formation time less than 90 seconds, means that the patient has an increased risk of experiencing a future cardiovascular event four to seven times more likely than if the platelet plug formation time is greater than or equal to 90 seconds.

In some embodiments platelet hyperactivity is evaluated using a high shear force test method or high shear platelet function test. In some embodiments of such a method, a platelet-containing sample from a patient is drawn under vacuum through a capillary and platelets are activated by means of shear force. The capillary is defined by its dimension and is generally a channel having a capillary dimension, i.e., a cross-sectional area that provides for capillary flow through the channel. At least one of the cross-sectional dimensions, e.g., width, height, diameter, is at least about 1 µm, or at least about 10 µm, and is usually no more than about 500 µm, or no more than about 200 µm. Channels of capillary dimension typically have an inside bore diameter (ID) of from about 1 to about 300 microns, or from about 10 to about 200 microns, or from about 25 to about 100 microns.

The capillary is manufactured from a material that is rigid or flexible, transparent or opaque. Particular plastics finding use for manufacturing of the capillary include, for example, flexible or rigid forms of polyethylene, polypropylene, polytetrafluoroethylene (PTFE), e.g., TEFLON®, polymethylmethacrylate, polycarbonate, polyethylene terephthalate, polystyrene or styrene copolymers, polyurethanes, polyesters, polycarbonates, polyureas, polyamides, polyethyleneamines, polyarylene sulfides, polysiloxanes, polydimethylsiloxanes, polyimides, polyacetates, poly etheretherketone (PEEK), and the like, either used alone or in conjunction with another material or materials.

Suitable rigid materials may include, for example, glass (which term is used to include silica), e.g., Bioglass, and rigid plastics and resins, metals such as, e.g., stainless steel, and so forth. Rigid plastics include, for example, polymers such as, e.g., poly (vinyl chloride), polyacrylamide, polyacrylate, polyethylene, polypropylene, poly(4-methylbutene), polystyrene, polymethacrylate, poly(ethylene terephthalate), nylon, poly(vinyl butyrate), etc., either used by themselves or in conjunction with other materials. The material chosen should not be reactive with the samples or reagents applied to the capillary.

The vacuum or negative pressure applied to the capillary is generally that which is effective or sufficient to subject the sample to high shear force. The term "high shear force" for purposes of the present disclosure means about 5000 to about 6000 reciprocal seconds or higher. Typically, the shear forces are those that are similar to shear forces of arteries and partially occluded blood vessels. The vacuum is usually about 1 to about 10 kPa, about 2 to about 9 kPa, about 3 to about 8 kPa, about 4 to about 7 kPa, or about 4 to about 6 kPa.

As a result of being subjected to a high shear force in the capillary, the platelets become activated. Activation of the platelets means that a conformational change occurs in the platelet glycoprotein GPIIb/IIIa receptor allowing it to bind fibrinogen and/or von Willebrand factor. It is this binding of the multivalent fibrinogen and/or von Willebrand factor molecules by GPIIb/IIIa receptors on adjacent platelets that results in the recruitment of additional platelets to a site of injury and their aggregation to form a hemostatic plug or thrombus.

In some embodiments a member is disposed with respect to an opening of the capillary. In many embodiments the member is absorbent to liquids so that agents capable of initiating the blood coagulation process or platelet aggregation in blood can be incorporated therein. The member may also have a stable structure so that a precise aperture can be placed through the member such as, for example, by being punched through the member. The member in some embodiments may also serve as a support matrix for a reagent such as, for example, a platelet aggregation stimulator, e.g. collagen.

As mentioned above, the member may be absorbent and thus may be a porous member. The pore size in preferred porous members is such that agents can penetrate the member and there is no interference with creating a negative pressure, e.g., in a test device, in order to aspirate blood through an aperture in the member as discussed hereinbelow. The pore size is also selected so that whole blood does not substantially penetrate the member but rather goes through an aperture in the membrane as discussed below.

The member may be disposed with respect to the capillary such that a surface of the member corresponding to a major dimension of the member is substantially transverse to the flow of the sample in the capillary. The term "substantially transverse" means that the surface of the member is within about 20 degrees from perpendicular, within about 15 degrees from perpendicular, within about 10 degrees from perpendicular, within about 5 degrees from perpendicular, within about 4 degrees from perpendicular, within about 3 degrees from perpendicular, within about 2 degrees from perpendicular, within about one degree from perpendicular, or perpendicular to the axis corresponding to the direction of flow of the sample in the capillary. The location of the member with respect to the capillary depends on a number of factors such as, for example, the length of the capillary, the diameter of the aperture, the nature of the sample, and the like. In some embodiments the member is located adjacent to an exit of the capillary, that is, an opening of the capillary through which the sample exits the capillary.

In some embodiments the member comprises a membrane. In some embodiments, as mentioned above, the membrane comprises an aperture, through which sample exiting the capillary may flow. The size of the aperture in the membrane is dependent on a number of considerations. The dimensions of the aperture are chosen such that under the conditions of the particular assay a plug will be formed and the opening closed. The aperture should not be so small that non-assay related blockages occur. The aperture should not be so large such that a plug does not form properly. For the platelet function test discussed herein, the aperture is between about 100 microns to about 200 microns, or about 140 microns to 160 microns, or about 150 microns. The dimension of the aperture in the member does not have a great influence on the initial flow characteristics in a device. Generally, the only passage for the sample exiting the capillary is through the aperture in the membrane.

The dimensions of the membrane are such that the diameter of the membrane is at least sufficient to adequately provide for formation of, and the presence of, an aperture as discussed above. Furthermore, as discussed below, the membrane may comprise a platelet aggregation stimulator incorporated therein or thereon. Accordingly, the diameter and thickness of the membrane is dependent on the amount of the platelet aggregation stimulator employed in a particular test. The dimensions of the membrane should be such that the membrane can comprise a sufficient quantity of the platelet aggregation stimulator.

The porous members provide a support matrix for the agent or agents that promote clotting or coagulation of blood. In some embodiments the porous member has absorbency to liquids so that reagents can be incorporated therein, yet has a stable structure so that a precise opening can be, for example, punched therein. The porous member is manufactured from a material that is able to maintain the size of the aperture therein even when wet. The material should be relatively inert to the agents used in the test and should not cause interfering activation of platelets or of the pathways. It should also be temperature insensitive at the temperature of the test, e.g., about 37° C. The membrane may be manufactured from, for example, cellulose esters such as, e.g., cellulose acetate, cellulose nitrate, and the like, ceramics, polymers such as, e.g., nylon, polypropylene, polyvinylidene fluoride (PVDF), and the like, glass such as, e.g., fiberglass, and so forth. In some embodiments the membrane is a mixed cellulose ester (acetate and nitrate) membrane from Millipore Corp., Bedford, Mass.

The porous members usually have incorporated therein, agents that allow direct and complete evaluation of platelet function and coagulation factors of blood. In many embodiments a membrane comprises a platelet aggregation stimulator, which is an agent that promotes aggregation of the platelets. Platelets are known to aggregate under a variety of conditions and in the presence of a number of different reagents. Platelet aggregation is a term used to describe the binding of platelets to one another. The phenomenon can be induced by adding aggregation-inducing agents to platelet-rich plasma (PRP) or to whole blood. Platelet aggregation in vitro depends upon the ability of platelets to bind fibrinogen and/or von Willebrand factor to their surfaces after activation by an aggregation-inducing agent such as ADP or collagen.

Examples of suitable platelet aggregation stimulators that may be employed in the present methods include collagen, ristocetin, arachidonic acid and the salts thereof, serotonin, adenosine-5'-diphosphate, epinephrine, thrombin, platelet activating factor (PAF), thrombin receptor agonist peptide (TRAP), and the like or combinations thereof such as, for example, collagen and adenosine-5'-diphosphate, collagen and epinephrine, and the like.

The platelet aggregation stimulator is bound to or within the membrane usually in a diffusive manner. In some embodiments the platelet aggregation stimulator is bound to the membrane non-covalently such as, for example, by means of adsorption, absorption, absorption and drying, and so forth.

In one embodiment a solution of platelet aggregation stimulator is contacted with the membrane to allow the membrane pores to absorb with the solution. Then, the membrane is removed from contact with the solution and dried.

The amount of the platelet aggregation stimulator on the membrane is that which is effective or sufficient to promote aggregation of the platelets in the sample under the conditions of the present methods. The amount employed depends on the nature of the platelet aggregation stimulator, the nature of the sample and the like. The amount of platelet aggregation stimulator is about 1 µg to about 100 µg, about 5 µg to about 80 µg, about 10 µg to about 70 µg, about 20 µg to about 60 µg, or about 30 µg to about 50 µg, and the like. In one embodiment the membrane comprises 50 µg of adenosine-5'-diphosphate and about 2 µg of collagen. By "diffusively bound" is meant that the platelet aggregation stimulator is bound to the membrane so that it will be removed from the membrane during the present method, usually, upon contact with, or exposure to, a sample being tested. The platelet aggregation stimulator may be incorporated in the membrane as a result of an ability to penetrate the membrane and, in some embodiments saturate the membrane, thereby forming a film on the membrane as well as being incorporated therein.

The high shear force test method or high shear platelet function test is usually conducted at moderate temperatures such as for example, about 25 to about 45° C., about 30 to about 40° C., about 37 to about 38° C., and so forth.

The time it takes to form, i.e., the time to formation of, a platelet plug that blocks the aperture is measured and related to hyperactivity of the platelets and, ultimately, to the risk of a patient undergoing aspirin antiplatelet therapy to experience an adverse cardiovascular event. In some embodiments the aperture is considered to be blocked when blood flow through the capillary has been reduced to 10% of its initial flow. The time period is generally measured from the point of application of vacuum to the capillary to the point of formation of a platelet plug that blocks the aperture. In some embodiments this time period is referred to as the closure time.

In some embodiments the time to formation of a platelet plug is compared to a predetermined time, and a time to formation of the platelet plug that is less than the predetermined time is indicative of an increased risk of the patient for an adverse cardiovascular event. In some embodiments the predetermined time is established as follows: perform platelet function testing with blood samples from patients taking aspirin and having cardiovascular disease. Using the results of the platelet function testing and adverse event information collected on the same population of patients over a time period of six months, one year or longer, construct a sensitivity-specificity graph as shown in FIG. 1 using receiver-operator curve (ROC) analysis. From the ROC curve, draw a line from the point termed "perfect" to the closest point on the curve. This point on the curve defines the optimum cut-off value or decision point or predetermined time of the test. In some embodiments the extent of the risk for an adverse cardiovascular event is directly related to the extent by which the time to formation of a platelet plug is less than the predetermined time.

In some embodiments the methods disclosed herein may be carried out using apparatus and reagents disclosed in U.S. Pat. No. 5,854,076, the relevant disclosure and figures thereof being incorporated herein by reference. In the embodiments in the above patent, the capillary and membrane are present in a test cartridge, which comprises a housing that defines a holding chamber and a test chamber. The housing may include a flange, a tab, and a removable top seal, which in the assembled device is hermetically sealed to the flange and closed at the bottom with a bottom seal. The test chamber is adapted to receive a sample cup. The sample cup supports a reagent treated porous member having an aperture therein and a capillary hub that provides a mechanism to operably attach the capillary to the sample cup. The interior of the sample cup may be provided with positioning means such as vacuum chuck stop ribs for positioning. The housing is adapted to mate with an instrument that can create a negative pressure in the test chamber or in a part of the test chamber. In one embodiment, this is accomplished by a rim of a sample cup, which comprises a part of the test chamber. The instrument has a mating component, which is capable of sealably mating with the rim of the sample cup. The mating component may comprise a vacuum chuck provided with O-ring, which during an assay sealably meets the rim. The vacuum chuck is moved by the instrument to contact the rim and to exert a downward pressure on the sample cup to move a capillary towards a pierceable member, causing it to pierce the pierceable member and extend into a sample in the holding chamber. The stop ribs in the sample cup of the vacuum chuck limit the downward movement of the vacuum chuck. Sample is caused to flow from the holding chamber to the test chamber by the negative pressure created by the instrument.

In some embodiments the methods disclosed herein may be carried out using the PFA-100® system (Dade Behring Inc., Deerfield, Ill.), which is an instrument and test cartridge system in which the process of platelet adhesion and aggregation following a vascular injury is simulated in vitro. This system allows for rapid evaluation of platelet function on samples of anticoagulated whole blood. Membranes consisting of Collagen/Epinephrine (CEPI) and Collagen/Adenosine-5'-diphosphate (CADP) and the high shear rates generated under standardized flow conditions, result in platelet attachment, activation and aggregation, building a stable platelet plug at the aperture in the membrane. The time required to obtain full occlusion of the aperture is reported as the closure time (CT) in seconds.

Kits can be employed for conducting any of the above methods. In the kit the reagents can be provided in packaged combination in the same or separate containers, depending on the cross-reactivity and stability of the reagents, so that the ratio of reagents provides for substantial optimization of a signal from the reporter molecule used in the detection system. The diagnostic kit can comprise in packaged combination one or more test cartridges comprising a capillary and membrane as discussed above. The kit may also include other reagents as may be employed in the tests.

EXAMPLES

The invention is demonstrated further by the following illustrative examples. Temperatures are in degrees Centigrade and parts and percentages used in this disclosure are by weight unless otherwise specified.

Methods

Patient group: A total of 326 consecutive patients were studied, all of whom had stable cardiovascular disease and were taking 325 mg of aspirin/day for at least 7 days. Of the 326 patients, 315 were available for follow-up. The focus of this investigation was aimed solely at those patients for whom aspirin therapy was considered effective using optical aggregation as defined in Gum, et al. [0.5 mg/mL arachidonic acid <20% and 10 µM ADP <70%]. By these criteria, 299 patients were included in the present study. However, only 296 patients had sufficient quantities of whole blood available to carry out PFA-100 testing. Complete details of this patient group were previously reported (Gum P A, Kottke-Marchant K, Poggio E D, Gurm H, Welsh P A, Brooks L, Sapp S K, Topol E J. Profile and prevalence of aspirin resistance in patients with cardiovascular disease. *Am J Cardiol.* 2001; 88:230-5. Gum P A, Kottke-Marchant K, Welsh P A, White J, Topol E J. A prospective, blinded determination of the natural history of aspirin resistance among stable patients with cardiovascular disease. *J Am Coll Cardiol.* 2003; 41:961-5). Pertinent demographic information is provided in Table 1 (below). The study was approved by the institutional review board and all patients gave informed consent. It is important to note that, although the previous database from Gum et al. was used in the studies above, the present methods and studies are not disclosed or suggested in Gum.

Blood samples and platelet function testing: Whole blood was collected in 3.8% buffered sodium citrate and testing was conducted as previously described. Briefly, high-shear platelet function testing was performed in duplicate with the PFA-100 (Dade Behring Marburg GmbH, Germany; employed as an investigational device in this patient group) using the CADP cartridge. The mean results of duplicate measurements were used in data analysis.

Statistical Analysis of Clinical Outcome: Differences in baseline characteristics between positive and negative hypersensitivity of platelets to ADP (HSPA) groups (see below) were determined by chi-squared analysis for dichotomous outcomes. For continuous outcomes, a Student's t-test was performed. An average of 22 months follow-up was obtained on patients enrolled in the study. Receiver Operator Characteristic (ROC) curves were used to generate decision thresholds (clinical cut-off values) for the platelet function tests. The best clinical performance of the assay is determined by finding the point on the curve that is closest to a "perfect" test (see FIG. 1). This led to the definition of HSPA as a patient having a CADP CT <90 seconds (Table 1). Relative risk (RR) values were then calculated for the composite events and the individual component events. Poisson regression was used to adjust for the effects of concomitant risk factors and evaluate HSPA status as an independent predictor of the composite outcome of death, MI, or CVA, as well as the individual components. Poisson regression was chosen for this purpose as it allows for presentation of the results in terms of RR's.

TABLE 1

Demographic characteristics of aspirin sensitive patients by HSPA status.

|  | Positive HSPA† (125/296) | Negative HSPA (171/296) | p value |
|---|---|---|---|
| Clinical Factors* | | | |
| Age (years) | 60 ± 10 | 61 ± 10 | 0.706 |
| Sex (% male) | 76.8 | 79.4 | 0.591 |
| Smoking (%) | 66.1 | 74.9 | 0.102 |
| Diabetes (%) | 32.0 | 29.2 | 0.610 |
| Prior CABG (%) | 43.2 | 36.3 | 0.227 |
| Prior PCI (%) | 38.4 | 33.9 | 0.427 |
| Prior MI (%) | 47.2 | 37.4 | 0.092 |
| Prior CVA (%) | 7.2 | 3.5 | 0.153 |
| CHF (%) | 10.4 | 2.9 | 0.008 |
| Laboratory values | | | |
| Hemoglobin (g/dL) | 14 ± 2 | 14 ± 1 | 0.746 |
| Platelet count (x10³/µL) | 217 ± 71 | 194 ± 64 | 0.003 |
| Ticlopidine/clopidogrel (%) | | | |
| Death/MI/CVA | 19.2 | 5.3 | <0.001 |
| Death (%) | 11.2 | 1.8 | 0.001 |
| MI (%) | 6.4 | 4.1 | 0.372 |
| CVA (%) | 4.0 | 0.6 | 0.040 |

*ASA = aspirin; CABG = coronary artery bypass grafting; CHF = congestive heart failure; CVA = cerebrovascular accident; MI = myocardial infarction; PCI = percutaneous coronary intervention.
†Defined by CADP CT <90 seconds.

Results

Criteria for HSPA: By ROC analysis, CADP CT significantly correlated with the composite endpoint of death, myocardial infarction or cerebrovascular accident (p<0.0001, FIG. 1). The cutoff established by the ROC analysis for HSPA was a CADP CT <90 seconds.

Prevalence of HSPA associated with major clinical events: HSPA patients (125/296=42.2%) had a composite endpoint rate of 19.2% (24/125) while non-HSPA patients (171/296=57.8%) only experienced events at a rate of 5.3% (9/171).

Future risk of a major clinical event: HSPA patients had a RR of 3.65 (95% C.I.: 1.76-7.57) for the composite endpoint (Table 2). The RR increased to 6.56 (95% C.I.: 1.93-22.35) for those patients who died compared to patients with CADP CT ≧90 seconds. The RR values in this subgroup for 10 μM ADP aggregometry ranged from 1.05 to 4.95 for the composite endpoint and the individual events of death, myocardial infarction and cerebrovascular accident, but were not statistically significant.

TABLE 2

Increased risk of experiencing major adverse clinical events as assessed by platelet function testing.

| Outcome | Group | Relative Risk (RR) | 95% C.I. for RR | Decision Threshold* (seconds) |
|---|---|---|---|---|
| All Events | PFA CADP | 3.65 | 1.76-7.57 | <90 |
| Death | PFA CADP | 6.56 | 1.93-22.35 | <90 |
| MI | PFA CADP | 2.61 | 0.85-8.00 | <96 |
| CVA | PFA CADP | 6.84 | 0.81-57.82 | <90 |

*Note: for MI and CVA the RR values were not statistically significant.

Validation of HSPA as an independent risk factor: Two multivariate analyses were presented for consideration in order to show that HSPA is not merely the byproduct of some spurious correlation, but is itself a risk factor for untoward events. For this end goal, Poisson regression was employed to estimate the relative risks relating the various outcome variables versus HSPA and other typical risk factors. However, the utility of these models is hampered when too many predictor variables are used. In order to limit the number of variables entered into the model, a Poisson regression was used to determine which risk factors were associated with HSPA, and thus could generate a spurious correlation between HSPA and the outcome variables of interest. This analysis found that platelet count and smoking were significantly associated with HSPA at the 0.05 level of significance (Table 3). Thus, it was only necessary to enter these variables into the statistical model to demonstrate the ability of HSPA to predict events, even after correcting for the effect of concomitant variables in the model (Table 4). HSPA was a significant predictor of the composite event and death. Though all RR estimates were greater than unity, HSPA generated statistically insignificant results with the outcomes MI and CVA.

TABLE 3

HSPA vs potential risk factors.

| Variable | p value |
|---|---|
| Platelet count | 0.045 |
| Smoking | 0.029 |
| Age | 0.437 |
| Hemoglobin | 0.131 |
| Diabetes | 0.197 |
| Prior CABG | 0.334 |

TABLE 3-continued

HSPA vs potential risk factors.

| Variable | p value |
|---|---|
| Prior PCI | 0.869 |
| Prior MI | 0.062 |
| Prior CVA | 0.617 |
| CHF | 0.149 |

TABLE 4

Relative risk for HSPA after correction for concomitant risk factors.

| Outcome | RR for HSPA (95% CI) | p value |
|---|---|---|
| dmcva* | 2.47 (1.11-5.48) | 0.026 |
| Death | 4.89 (1.36-17.52) | 0.015 |
| MI | 1.18 (0.41-3.38) | 0.762 |
| CVA | 3.30 (0.36-30.69) | 0.293 |

*Composite event: death, MI or CVA (dmcva).

Discussion

The current study focused on results not previously evaluated using ROC analysis to assess HSPA and clinical outcomes specifically in the aspirin sensitive subgroup of patients. Thus, despite apparently therapeutic aspirin, patients experienced significantly increased risk of subsequent major adverse events if their CADP CT was <90 seconds. This held true when all patients (aspirin sensitive and aspirin resistant) were considered together where the RR for composite events was 2.88 (95% C.I.: 1.50-5.52) and for death was 5.32 (95% C.I.: 1.81-15.66) (data not shown). Additionally, the multivariate analyses support HSPA as an independent predictor of mortality rather than being merely a proxy for other risk factors.

The CADP CT correlated with the composite events in a manner that appears to be independent of the presence of aspirin. This observation is consistent with the general insensitivity of the CADP cartridge for platelet inhibition induced by aspirin and suggests that CADP CT is detecting an underlying ADP-dependent platelet hypersensitivity that is clinically significant.

The negative predictive value (NPV) of CADP CT for the composite and individual events ranged from 94.7% to 99.4%, respectively (Table 5). Not surprisingly, the positive predictive values (PPV) were low (<20%), while sensitivity and specificity ranged from 73% to 83% and 50% to 62%, respectively. This suggests that measurement of HSPA has high exclusionary predictive value for adverse clinical events in coronary patients.

TABLE 5

Clinical performance of platelet function testing for major adverse clinical events.

| Outcome | Sensitivity % | Specificity % | PPV % | NPV % |
|---|---|---|---|---|
| All Events | 72.7 | 61.6 | 19.2 | 94.7 |
| Death | 82.4 | 60.9 | 11.4 | 98.3 |
| MI | 73.3 | 49.8 | 7.2 | 97.2 |
| CVA | 83.3 | 58.6 | 4.0 | 99.4 |

SUMMARY

Notwithstanding the clinical importance of detecting the antiplatelet response to aspirin, underlying hypersensitivity to ADP appears to exist in some patients with stable cardiovascular disease that significantly increases their risk for major adverse clinical events. HSPA appears to be unaffected by therapeutic aspirin and is detectable by ADP-dependent processes that can be measured by the PFA-100® System using the CADP cartridge. This study intentionally focused only on those patients defined as aspirin sensitive by previously established criteria of arachidonic acid- and ADP-induced platelet aggregometry. Follow up averaged 22 months for the adverse clinical events of death, myocardial infarction or cerebrovascular accident. Patients with CADP CT <90 seconds (125/296=42.2%) had a composite endpoint rate of 19.2% (24/125), while those with CADP CT $\geq$90 seconds (171/296=57.8%) had an endpoint rate of 5.3% (9/171). Patients with CADP CT <90 seconds had a relative risk (RR) of 3.65 (95% C.I.: 1.76-7.57) for recurrent events and 6.56 (95% C.I: 1.93-22.35) for death compared to patients with CADP CT $\geq$90 s.

Platelet function testing in accordance with the present methods, using the PFA-100® System as an exemplary system, appears to identify a subgroup of stable cardiovascular disease patients with increased risk of major adverse events that is associated with hypersensitivity to ADP, regardless of apparently effective aspirin therapy.

All publications and patents mentioned in this specification are indicative of the level of skill of those skilled in the art to which this invention pertains. All publications and patent applications are herein incorporated by reference to the same extent as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A method for identifying a patient having an increased risk of an adverse cardiovascular event wherein the patient is undergoing aspirin antiplatelet therapy, said method comprising:
    (a) evaluating a platelet-containing sample from the patient for platelet hyperactivity wherein the patient is aspirin sensitive, which is defined as a patient for whom aspirin therapy is considered effective as determined by an optical aggregation method utilizing arachidonic acid-induced and ADP-induced platelet aggregometry and
    (b) relating platelet hyperactivity in the sample to the patient's risk of an adverse cardiovascular event.

2. A method according to claim 1 wherein the evaluating of step (a) is carried out by assessing the function of platelets in the sample using a high shear platelet function test.

3. A method according to claim 1 wherein platelet function is assessed by a high shear platelet function test using a platelet aggregation stimulator.

4. A method according to claim 3 wherein the platelet aggregation stimulator is selected from the group consisting of collagen, ristocetin, arachidonic acid, serotonin, adenosine-5'-diphosphate, epinephrine, and thrombin and combinations thereof.

5. A method according to claim 4 wherein the platelet aggregation stimulator is collagen and adenosine-5'-diphosphate.

6. A method according to claim 1 wherein the sample is drawn under vacuum through a capillary so that it contacts a membrane comprising an aperture and platelets in the sample are activated by means of shear force and the time to formation of a platelet plug that blocks the aperture is measured and related to the increased risk of an adverse cardiovascular event in the patient.

7. A method according to claim 6 wherein the membrane comprises a platelet aggregation stimulator.

8. A method according to claim 7 wherein the platelet aggregation stimulator is selected from the group consisting of collagen, ristocetin, arachidonic acid, serotonin, adenosine-5'-diphosphate, epinephrine, and thrombin and combinations thereof.

9. A method according to claim 7 wherein the platelet aggregation stimulator is collagen and adenosine-5'-diphosphate.

10. A method according to claim 1 wherein the platelet-containing sample is whole blood.

11. A method for assessing the risk of an adverse cardiovascular event in a patient undergoing antiplatelet aspirin therapy, said method comprising:
    (a) drawing a platelet-containing sample from the patient under vacuum through a capillary so that it contacts a membrane comprising an aperture and platelets in the sample are activated by means of shear force, wherein the membrane comprises a platelet aggregation stimulator and wherein the patient is aspirin sensitive, which is defined as a patient for whom aspirin therapy is considered effective as determined by an optical aggregation method utilizing arachidonic acid-induced and ADP-induced platelet aggregometry,
    (b) measuring the time to formation of a platelet plug that blocks the aperture of the membrane, and
    (c) relating the time to formation of the platelet plug to the patient's risk of an adverse cardiovascular event.

12. A method according to claim 11 wherein the platelet aggregation stimulator is selected from the group consisting of collagen, ristocetin, arachidonic acid, serotonin, adenosine-5'-diphosphate, epinephrine, and thrombin and combinations thereof.

13. A method according to claim 11 wherein the platelet aggregation stimulator is collagen and adenosine-5'-diphosphate.

14. A method according to claim 11 wherein the platelet-containing sample is whole blood.

15. A method according to claim 11 wherein the time to formation of a platelet plug is compared to a predetermined time and a time to formation of a platelet plug less than the predetermined time is indicative of an increased risk of the patient for an adverse cardiovascular event.

16. A method for assessing the risk of an adverse cardiovascular event in a patient undergoing antiplatelet aspirin therapy, said method comprising:
    (a) drawing a whole blood sample from the patient under vacuum through a capillary so that it contacts a membrane comprising an aperture and platelets in the sample are activated by means of shear force, wherein the membrane comprises a platelet aggregation stimulator and wherein the patient is aspirin sensitive, which is defined as a patient for whom aspirin therapy is considered effective as determined by an optical aggregation method utilizing arachidonic acid-induced and ADP-induced platelet aggregometry, (b) measuring the time to formation of a platelet plug that blocks the aperture of the membrane, and (c) relating the time to formation of the platelet plug to the patient's risk of an adverse cardiovascular event wherein the time to formation of a platelet plug is compared to a predetermined time and a time to formation of a platelet plug less than the predetermined time is indicative of an increased risk of the patient for an adverse cardiovascular event.

17. A method according to claim 16 wherein the platelet aggregation stimulator is selected from the group consisting of collagen, ristocetin, arachidonic acid, serotonin, adenosine-5'-diphosphate, epinephrine, and thrombin and combinations thereof.

18. A method according to claim 16 wherein the platelet aggregation stimulator is collagen and adenosine-5'-diphosphate.

* * * * *